United States Patent [19]
DiLorenzo

[11] Patent Number: 5,797,403
[45] Date of Patent: Aug. 25, 1998

[54] METHOD FOR REDUCTION OF NEUROSURGICAL EDEMA, HEMORRHAGE, AND RESPIRATION-INDUCED TISSUE MOVEMENT

[76] Inventor: Daniel J. DiLorenzo, 148 Allston St., Cambridge, Mass. 02139

[21] Appl. No.: 581,166

[22] Filed: Dec. 29, 1995

[51] Int. Cl.$^6$ ..................................................... A61B 19/00
[52] U.S. Cl. ........................... 128/856; 128/849; 604/28
[58] Field of Search ..................................... 128/849, 856, 128/853; 604/118, 28; 600/21; 602/2, 60, 61, 62, 63

[56] References Cited

U.S. PATENT DOCUMENTS

| | | | |
|---|---|---|---|
| 4,024,872 | 5/1977 | Muldoon | 128/856 X |
| 4,275,719 | 6/1981 | Mayer | 128/849 X |
| 4,340,043 | 7/1982 | Seymour | 128/849 |
| 4,865,049 | 9/1989 | Gatti | 128/849 |
| 4,998,538 | 3/1991 | Charowsky et al. | 128/856 |
| 5,178,162 | 1/1993 | Bose | 128/856 X |
| 5,316,541 | 5/1994 | Fischer | 128/849 X |
| 5,568,817 | 10/1996 | Harty | 128/849 |

*Primary Examiner*—Sam Rimell

[57] ABSTRACT

An intraoperative and perioperative method and several representative apparatus designs therefor for the reduction of fluid and tissue movement, where said fluid includes but is not limited to plasma, extracellular fluid, intracellular fluid, cerebrospinal fluid, and blood; and said tissue includes but is not limited to central nervous system tissue. An application of particular import in neurosurgical procedures is the intraoperative control of cerebral and spinal cord edema and the reduction of respiration-induced tissue movement. The method of the present invention, as applied to neurosurgical edema reduction, involves control of the pressure gradient between the central nervous system (CNS) and the ambient pressure. The physiologic pressure gradient between the CNS and the ambient pressure is termed the intracranial pressure (ICP) and is normally maintained at approximately 14 mmHg. The ICP may be decreased, normal, or increased as a result of any of various pathologic conditions which may indicate neurosurgical intervention. A significant complication of neurosurgical procedures is edema of the exposed nervous tissue. Control, including reduction and/or reversal, of the CNS-ambient pressure gradient eliminates the hydrostatic contribution to the generation of cerebral edema. By appropriate modulation of the applied pressure gradient, the dynamic component of the intracranial-ambient pressure gradient associated with respiration is canceled, reducing or eliminating intraoperative tissue movement. This is of particular utility in microneurosurgical procedures and in neurosurgical procedures involving placement of electrodes. The apparatus facilitates the control of the pressure gradient between the CNS and the ambient pressure and may be implemented as any of numerous possible equivalent designs, two representative embodiments including (1) a hypobaric chamber applied to a section of the unopened portion of the calvarum and extending to include the entire caudal portion of the body and (2) a hyperbaric chamber affixed to the head to apply pressure to the exposed cerebral surface. The method and apparatus of the present invention are additionally efficacious in the control of edema in other surgical procedures. Furthermore, the method and apparatus of the present invention are effective in the control of hemorrhage.

2 Claims, 13 Drawing Sheets

METHOD FOR REDUCTION OF NEUROSURGICAL EDEMA, HEMORRHAGE, AND RESPIRATION-INDUCED TISSUE MOVEMENT

BACKGROUND OF THE INVENTION

A. Field of the Invention

The present invention has relation generally to method and apparatus for intraoperative and perioperative pressure gradient regulation, and more particularly to control of pressure gradients across operatively exposed tissues, fluids or other natural or artificial components, including but not limited to the dura and blood vessels, for the reduction of at least one of edema, hemorrhage, and tissue movement.

B. Underlying Physiology and Current State of the Art

This invention relates to several intraoperative and perioperative conditions and complications which may be amenable to treatment or prevention by the controlled application of a pressure gradient across the operatively exposed tissue or structures. This invention has application to neurosurgical procedures, general surgical procedures, orthopedic surgical procedures, and other major and minor surgical procedures in the control of at least one of edema (excessive accumulation of watery fluids is cells, tissues, or serious cavities), hemorrhage, and tissue movement.

B1. Edema, Particularly as Encountered Intraoperatively in Neurosurgery

Edema commonly occurs during and following surgical procedures. Edema in central nervous system (CNS) structures is of particular concern because negligible room for expansion is permitted by the virtually inelastic dura which envelopes the CNS and the bony calvarum to which the dura is attached. For simplicity, "cerebral edema" will be understood to refer to and encompass edema of any and all parts of the CNS and peripheral nervous system (PNS), including but not limited to the cerebrum, cerebellum, brainstem, spinal cord, nerve roots, dorsal root ganglia, spinal nerves, cranial nerves, and peripheral nerves.

Central nervous system tissue is physiologically maintained at a pressure greater than the extracranial pressure, which is typically that of the ambient room pressure. This is influenced by several factors, including rates of production and outflow of cerebrospinal fluid (CSF), carotid arterial and jugular venous pressures, vasomotor tone of CNS arterioles, oncotic and osmotic pressures of the serum, and permeability of the vascular endothelial cells. These factors are further modulated by local and systemic parameters, exemplified by hormones, arterial carbon dioxide partial pressure, inflammatory cytokines, surgical or accidental trauma to vascular endothelial cells, and release of intracellular contents by damaged cells.

The pressure within the normal intact CNS is substantially uniform, and the intracranial-ambient pressure gradient is borne by the dura and surrounding bony structures. During neurosurgical procedures, the dura, subsequent to incision, becomes incapable of maintaining the tension along its curved plane required to balance the pressure difference between its internal and external surfaces. Consequently, this pressure gradient must be borne by a volume of CNS tissue, that including, surrounding, and deep to the exposed surface.

This pressure gradient may cause mechanical deformation of the CNS tissue as well as fluid shifts, from the intravascular space to the extracellular space. Fluid may shift within the extracellular space along this pressure gradient, with flow proceeding from the deeper regions to the more superficial. Furthermore, the hydrostatic-oncotic pressure balance between the intravascular space and the extracellular space is disturbed, and a fluid driving pressure gradient is established from the intravascular to the extracellular space, producing edema from plasma-derived fluid.

These fluid shifts can result in significant accumulation of fluid, i.e. edema, of the exposed and underlying tissue, with several undesirable effects. The excessive fluid volume in the edematous tissue causes compression of the vascular space and can result in ischemia. Ischemia, in turn, by compromising cell metabolism, impairs ionic transport across cell membranes; net sodium influx results, drawing water with it into the intracellular space; this cell swelling further exacerbates the edema. The increase in tissue volume can present a serious problem to the surgeon at the completion of the neurosurgical procedure.

Normally, the virtually inelastic dura is reapposed over the nervous tissue, and the bone flap is replaced prior to skin closure. If the volume of the tissue has increased, as occurs in edema, closure of the increased tissue volume within the unchanged volumes contained by the dura and cranial vault will necessarily result in an increase in intracranial pressure. Postoperative persistence of elevated ICP is associated with increased morbidity and mortality.

Intraoperative options available to the neurosurgeon include (1) resection of otherwise viable nervous tissue to compensate for the volume increase resulting from edema, (2) withdrawal of cerebrospinal fluid (CSF) from the ventricles for the same purpose, and (3) closure of the skin over the dura without replacement of the bone flap. These options are suboptimal, resulting in potentially decreased postoperative neurological function, incomplete decompression, and potential need for reoperation, respectively.

Pharmacological means are used to reduce cerebral edema in an effort to reduce intracranial pressure (ICP) in the preoperative, intraoperative, and postoperative periods. Neurosurgical procedures are not uncommonly delayed while awaiting a drop in the intracranial pressure in response to preoperative administration of pharmacological agents. The major drugs currently used include diuretics, steroids, osmotic agents, and short-acting barbiturates. Other modalities of prevention or treatment include cerebrospinal fluid drainage (via ventricular catheter), hypothermia, assisted ventilation with hyperventilation, dehydration, and avoidance of cerebral vasodilating anesthetics. These agents, though helpful, often provide incomplete reduction of intracranial pressure and may take hours to days to achieve requisite decompression.

B2. CSF Loss Encountered Intraoperatively in Neurosurgery

The intracranial-ambient pressure gradient may cause flow and leakage of CSF through the operative incision. Loss of CSF from the region of the spinal cord can result in caudal shift of the brain with impingement against bony or fibrous structures in the head. These include herniation of the uncus through the tentorium and herniation of the cerebellar tonsils or the brainstem through the foramen magnum. Consequences can range from headache to death, depending on the magnitude of the shift and the structures compromised.

B3. Edema in Other Surgical Procedures

Edema occurs during and following other surgical procedures and may also be undesirable. Edema is a well known complication of general surgical procedures. Intraoperative and postoperative shift of fluid from the intravascular space to the extracellular space is termed "third spacing", and this typically involved several liters of fluid. Consequently, several liters of intravenous fluids are given intraoperatively and in the early postoperative period to minimize hypovolemia and cardiovascular compromise. This edema fluid is subsequently remobilized back to the intravascular space, typically on the third postoperative day, and poses a risk of hypervolemia, including such complications as atrial fibrillation. Careful monitoring of patient fluid status and adjustment of intravenous and oral fluid intake to minimize perioperative and postoperative intravascular volume excursions is the current practice, and this affords a limited control with a slow time response in the fluid management of the surgical patient.

B4. Hemorrhage, Particularly Intraoperative and Postoperative

Intraoperative and postoperative hemorrhage is undesirable yet common. The shift of blood out of the intravascular compartment is driven by the pressure gradient between a combination of the systolic and diastolic blood pressures and the surrounding ambient pressure or that of any body cavity or potential space into which the hemorrhage may occur. Hemorrhage preoperatively or in the absence of surgery is a concern as well, particularly in cases involving trauma. The major methods currently used to control hemorrhage include blood vessel ligation and electrocautery. Tourniquets may also be used to arrest hemorrhage from distal portions of the body.

B5. Tissue Movement, Particularly that of the Nervous System

During neurosurgical procedures, the exposed brain or spinal cord is observed to move in a cyclical manner with respiration or mechanical ventilation. This movement limits the accuracy and expediency of microsurgical procedures. Fine surgical manipulation can be compromised by movement of the tissue, focal plane of the surgical microscope. Changes in intrathoracic pressure are transmitted via the vascular system to the CNS tissue; this is evidenced by the cyclic fluctuation of the intracranial pressure, as measured through a ventricular catheter in an otherwise intact subject, in association with the respiratory cycle. Intraoperatively, when a portion of the CNS is exposed to ambient pressure, the ICP pressure gradient effects movement of the CSF and the CNS tissue. The edematous effects of the static component of the pressure gradient are described previously. This static component also causes a shift in the position of the tissue, particularly in spinal surgery. The dynamic component of this pressure gradient effects intraoperative movement of CNS tissue in association with respiration and to a lesser extent with the cardiac cycle. This presents difficulty in surgical manipulation, tissue visualization, placement of implanted electrodes or other devices, and in positioning of neurophysiological electrodes. These problems are encountered in human and animal procedures, in both clinical evaluation and research experimentation.

C. Summary of the Prior and Related Art

The prior art includes several different methods and apparatuses for the application of hyperbaric and hypobaric pressure to a subject. Such devices include so called depurators which apply a hypobaric pressure to the body of the subject; these systems are claimed to treat various diseases for which high altitude environments are claimed to be therapeutic. Other devices which apply pressure to regions of the body include enclosures designed to provide a sterile surgical field within a contaminated environment such as a battlefield. Yet other devices facilitate the application of pressure at the site of a wound for the purposes of hemostasis.

Despite the technology taught by such inventions, there remains a need for an invention which creates controlled pressure gradients across relevant anatomy to facilitate control of the movement of fluids and tissues while simultaneously permitting surgical intervention. A pronounced need for such a device exists in the field of neurosurgery. The edema which results from such uncontrolled fluid shifts causes postoperative elevation of intracranial pressure, a postoperative condition directly associated with increased morbidity and mortality. Other surgical procedures, particularly general surgical operations, have a need for intraoperative and postoperative control of fluid shifts. Considerable effort in the postoperative management of general surgical patients is directed toward the monitoring and control of intravascular and extracellular fluid volumes. These is a need for an invention which allows for intraoperative and postoperative control of these fluid shifts. Intraoperative, postoperative and post traumatic hemorrhage is a problem which remains in want of a better solution. Arrest of blood flow from compromised vessels may be technically difficult due to limited exposure of bleeding vessels, and the localization of the source of blood loss may be limited by the impaired visualization inherent in a bloody field. A clear need exists for an invention which facilitates manipulation of the intravascular-ambient pressure gradients and thereby allows for control or elimination of blood loss.

BRIEF DESCRIPTION OF THE INVENTION

A. Objects of the Invention

The present invention relates to the control of pressure gradients involved in the shift of CSF, intravascular fluid, extracellular fluid, blood, or other fluids. By controlling, reducing, eliminating, reversing, or modulating these pressure gradients, edema, hemorrhage, CSF loss, and tissue movement may be controlled and reduced. It is a general object of the present invention to provide a method and requisite apparatus for the manipulation of pressure gradients to effect control of the many types of fluid shifts that occur intraoperatively, preoperatively, postoperatively, or post-traumatically. It is a related general object of the present invention to provide a method and necessary apparatus for the performance of surgical procedures in which manipulation of pressure gradients is used to effect control of the many types of fluid shifts that occur intraoperatively, preoperatively, postoperatively, or post-traumatically.

A1. Objects Pertaining to Neurosurgery

It is an object of the present invention to provide a method and apparatus for performing a neurosurgical procedure with reduced or absent edema of the nervous tissue. It is another object of the present invention to provide a method and apparatus for performing a neurosurgical procedure with reduced or absent hemorrhage. It is yet another object of the present invention to provide a method and apparatus for performing a neurosurgical procedure with reduced or absent loss of cerebrospinal fluid. It is still another object of the present invention to provide a method and apparatus for performing a neurosurgical procedure with reduced or absent intraoperative movement of the nervous tissue.

A2. Objects Pertaining to Surgery in General

It is an object of the present invention to provide a method and apparatus for performing a surgical procedure with reduced or absent edema of the tissue within, surrounding, and remote from the operative zone. It is another object of the present invention to provide a method and apparatus for performing a surgical procedure with reduced or absent hemorrhage. It is still another object of the present invention to provide a method and apparatus for performing a surgical procedure with reduced or absent intraoperative movement of the operative tissue.

Other objects and advantages will be in part indicated in the following description and in part rendered apparent therefrom in connection with the annexed drawings.

B. Summary of the Invention

The present invention is a method and apparatus involving manipulation of pressure gradients to control the intraoperative, perioperative, or post-traumatic shifts of bodily fluids and tissues, including but not limited to the CSF, intravascular fluid, extracellular fluid, blood, and nervous tissues. By reducing, eliminating, reversing, modulating, or otherwise regulating these pressure gradients, edema, hemorrhage, CSF loss, and tissue movement may be controlled and reduced.

The method and apparatus of the present invention prescribe and effect, respectively, control of the pressure gradient between that of the bodily tissues and the ambient environment. The pressures within bodily fluids and tissues, exemplified by blood pressure and intracranial pressure, exceed that of the ambient environment. When the mechanical or functional integrity of these or the overlying tissues or structures is compromised, as is often the case during the intraoperative perioperative, and post-traumatic intervals, fluids otherwise normally contained by these structures may experience a net flow in response to these pressure gradients. These flows may be reduced, prevented, reversed, or otherwise controlled by the manipulation of these pressure gradients, as put forth in the method and effected by the apparatus of the present invention.

The method includes the application of this pressure gradient control to all bodily tissues, fluids, and natural or artificial structures, including but not limited to the nervous system, heart, limbs, thorax, abdomen, and implanted or explanted devices.

This method and requisite apparatus have application in neurosurgical procedures, in which incision of the dura exposes the nervous tissue to ambient, typically atmospheric, pressure. The nervous tissue is normally maintained at the intracranial pressure (ICP), typically 14 mmHg, and upon incision of the dura, this pressure gradient is borne by the nervous tissue. The resulting mechanical distension and edema are described previously. By the method of the present invention, this manipulation of this pressure gradient affords control, including reduction and elimination, of these untoward processes. Elimination of this pressure gradient, according to the method of the present invention, could be effected by increasing the ambient pressure to that of the ICP, by decreasing the ICP to ambient pressure, or a combination of ambient pressure and ICP manipulation.

This method and essential apparatus further have application in the control of hemorrhage in other surgical procedures. Hemorrhage results when the integrity of the vascular walls is compromised such that the vascular structures are incapable of sufficiently resisting the flow of blood along the intravascular-ambient pressure gradient. By the method of the present invention, manipulation of this pressure gradient affords control, including reduction and elimination, of hemorrhage. Elimination of this pressure gradient, according to the method of the present invention, could be effected by increasing the ambient pressure to that of the systolic, diastolic, or a function involving the two blood pressures, by decreasing any of these blood pressures to ambient pressure, or a combination of ambient pressure and blood pressure manipulation.

This method and required apparatus have further application in the intraoperative control of tissue or fluid movement. The oscillating pressure gradient associated with the respiratory cycle is transmitted from the thoracic cage via vascular structures to generate an oscillatory component of the intracranial pressure. During intraoperative exposure of the nervous system, this oscillating intracranial-ambient pressure gradient causes movement of the nervous tissues and the cerebrospinal fluid. By the method of the present invention, manipulation of this oscillatory pressure gradient affords control, including reduction and elimination, of this movement of tissues and fluids and other natural or artificial structures. Elimination of this pressure gradient, according to the method of the present invention, could be effected by cyclically increasing the ambient pressure to that of the intracranial pressure or the oscillating component thereof, by decreasing the intracranial pressure or the cyclical component thereof to ambient pressure, or a combination of ambient pressure and intracranial pressure manipulation. Elimination of this pressure gradient, according to the method and achieved by the apparatus of the present invention, is accomplished by manipulating at least one of the ambient pressure or the intracranial pressure to cancel or reduce at least one of the static (steady) or dynamic (oscillating) components of the intracranial-ambient pressure gradient.

The apparatus according to the present invention accomplishes at least one of the previously described methods. The present invention is characterized by an apparatus which controls the tissue-ambient pressure gradient by applying elevated pressure to a region including the zone of operation or trauma. The present invention is similarly characterized by an apparatus which controls the tissue-ambient pressure gradient by effecting reduced pressure in the tissue underlying, surrounding, or comprising a region of tissue excluding the zone of operation or trauma. The present invention is further characterized by an apparatus which controls the tissue-ambient pressure gradient by a combination of applying elevated pressure to a region including the zone of operation or trauma and effecting reduced pressure in the tissue underlying, surrounding, or comprising a region of tissue excluding the zone of operation or trauma.

BRIEF DESCRIPTION OF THE DRAWINGS

The present invention may be more clearly understood from a reading of the following detailed description in conjunction with the accompanying drawings wherein.

DETAILED DESCRIPTION OF THE INVENTION

In FIGS. 1 through 6, the underlying methods of the present invention are described, and in FIGS. 7 through 13, the apparatus by which the methods are conducted are described.

Figure 1:
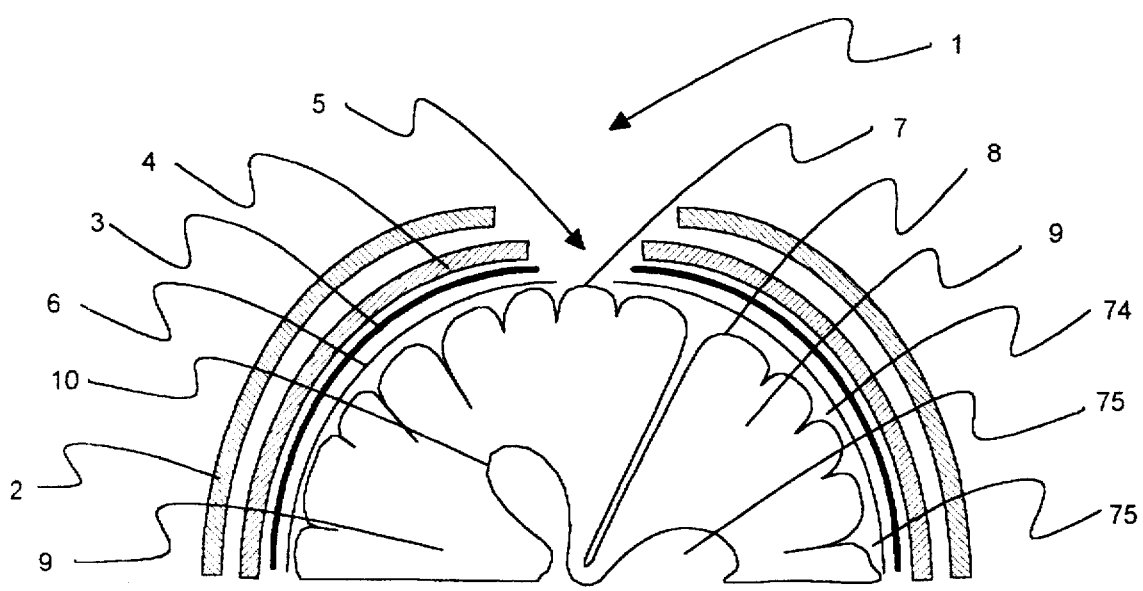
FIG. 1 is a coronal cross section of the brain and a craniotomy.

In FIG. 1, the anatomy pertinent to a craniotomy is shown and is used to illustrate the limitations of the current techniques. The operative zone ambient environment 1 typically consists of air at atmospheric pressure. The scalp 2 is the outer covering of the head. The calvarum 4 is deep to the scalp and forms the protective rigid covering of the brain. The dura 3 is the next layer deep to the calvarum 4. The arachnoid 6 is the next deep layer, enclosing the subarachnoid space 74. Deep to the arachnoid 6 is the normally unexposed cortical surface 8. The cortical surface is intimately lined by the pia layer which is not depicted here. The operatively exposed cortical surface 7 is deep to the region of the craniotomy 5 in which the calvarum 4 has been removed to permit entry to the underlying structures. The internal portion of the brain or brain parenchyma 9 lies deep to the cortical surface 8 and surrounds the fluid filled ventricles 10. The cerebrospinal fluid 75 is produced within the ventricles 10 and flows to the subarachnoid space 74.

All the structures deep to the calvarum 4 are normally maintained at the intracranial pressure (ICP), which is typically 14 mmHg above the ambient pressure. The calvarum 4 and dura 3 normally provide the mechanical tension to contain the neural tissue against the said pressure gradient. When the cortical surface 7 is exposed during a neurosurgical procedure or trauma, the pressure gradient is borne by the exposed cortical surface 7 and a portion of the underlying brain parenchyma 9. As described in previous sections, this hydrostatic pressure gradient drives fluid shifts from the intravascular space and the deeper extracellular space in the deeper regions of the brain parenchyma 9 to the extracellular space in the exposed cortical surface 7 and other exposed portions of the nervous tissue.

These fluid shifts commonly encountered in neurosurgical procedures result in tissue swelling or edema, and reduction or elimination of this edema is one of the objects of the present invention. The said edema is driven by the pressure gradient between the intracranial pressure and that of the operative zone ambient environment 1. A method of reduction of the said edema according to the present invention is the reduction of the said pressure gradient. This method may be accomplished by at least one of increasing the pressure in the operative zone ambient environment 1, decreasing the intracranial pressure, or a combination.

Figure 2:
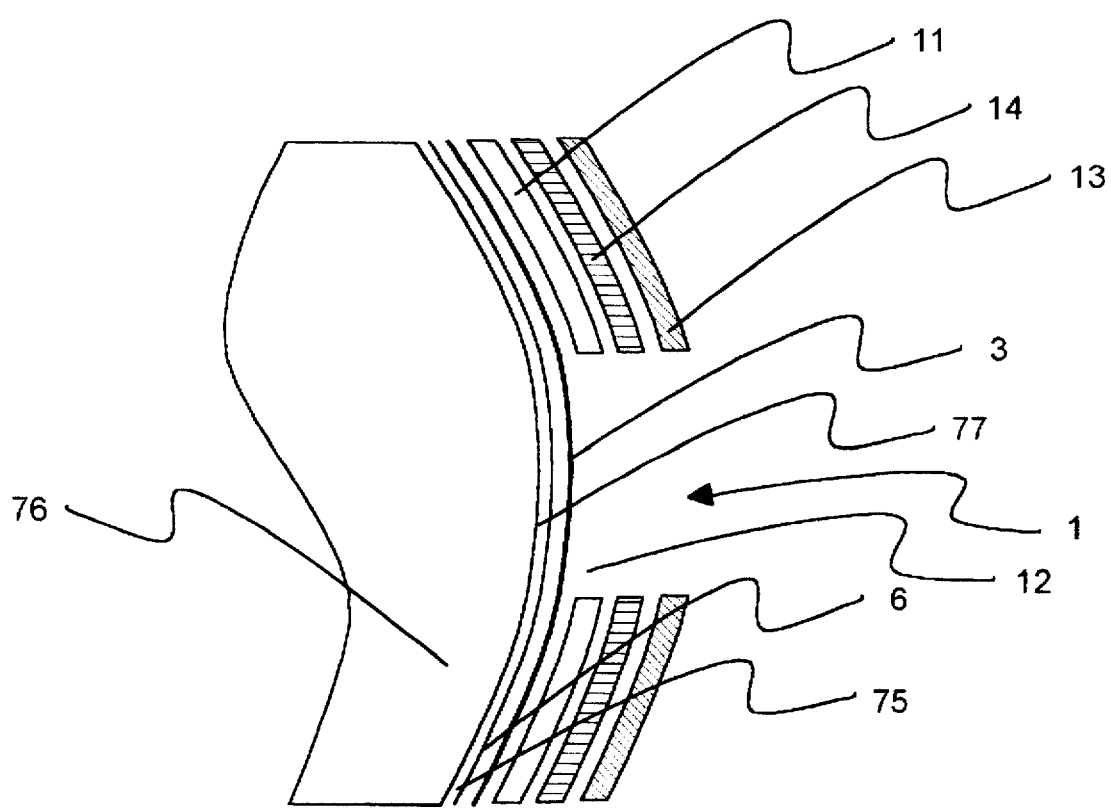
FIG. 2 is a horizontal cross section of the spinal cord and a laminectomy.

FIG. 2 is a horizontal cross section of the surface of the spinal cord. The operative zone ambient environment 1 is in contact with the exposed tissues, including most superficially the skin 13, the subcutaneous tissues 14. The bony structure comprised by the vertebral lamina 11 protect the underlying dura 3, arachnoid 6, and spinal cord 76. The vertebral lamina 11 are removed in the region of the laminectomy 12. As is the case in the craniotomy 5 shown in FIG. 1, when the spinal cord surface 77 is exposed to the operative zone ambient environment 1, the normally present pressure gradient can drive fluid from the spinal cord parenchyma 76 to the spinal cord surface 77, causing edema. Additionally, cyclic variation in the pressure of the CSF 75 which bathes the spinal cord surface 77 can cause movement of the spinal cord parenchyma 76 and said spinal cord surface 77 relative to the vertebral lamina 11, making fine surgical manipulation and visualization under a surgical microscope difficult, as described previously.

Figure 3:
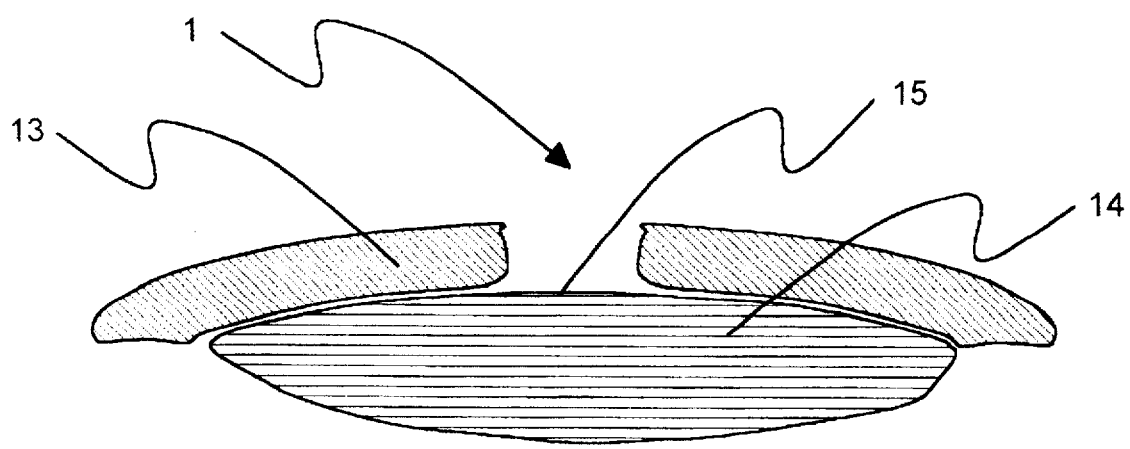
FIG. 3 is a cross section of a skin incision and underlying subcutaneous tissue.

FIG. 3 is a cross section of an incision onto the skin 13 overlying any portion of the body. The subcutaneous tissue 14 lies deep to the skin 13 and comprises muscle, adipose, or other tissue types. The subcutaneous tissue exposed surface 15 is in contact with the operative zone ambient environment 1. Muscles and other subcutaneous tissue components are maintained at a compartmental pressure in excess of that of the ambient environment. The pressure gradient between the compartmental pressure and that of the overlying operative zone ambient environment 1 are borne by the portions of the subcutaneous tissue 14 deep to and including the subcutaneous tissue exposed surface 15. This pressure gradient can cause fluid shifts from the intravascular space and the deeper portions of the extracellular space to the extracellular space in the region of the subcutaneous tissue exposed tissue 15, resulting in edema.

The pressure differences between the arterial and venous pressures and that of the operative zone ambient environment 1 may be termed the operative zone transarterial pressure gradient and operative zone transvenous pressure gradient, respectively; and these said gradients may be collectively referred to as operative zone transvascular pressure gradients. If the continuity of the vascular walls is compromised, the transvascular pressure gradients will drive blood flow through the damaged vascular walls, resulting in hemorrhage.

Figure 4:
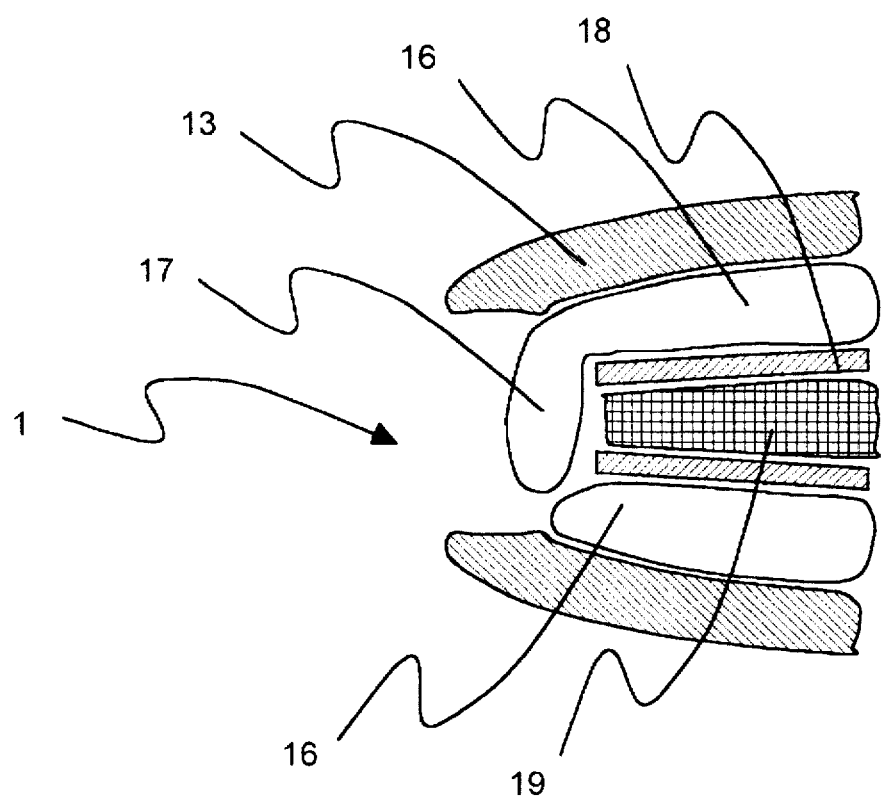
FIG. 4 is a cross section of a limb undergoing amputation.

FIG. 4 is a cross section of a limb during an amputation procedure. The operative zone ambient environment 1 is in contact with the skin 13 and the other exposed structures, including muscle 16, and the muscle flap 17 overlying the terminal portion of the limb including the bone 18 and bone marrow 19 contained therein. Transection of large and small blood vessels and exposure of the bone marrow 19 to the operative zone ambient environment 1, which is normally at a pressure much lower than the arterial or venous pressures, can result in significant hemorrhage. By controlling the transvascular pressure gradients, by at least one of increasing the pressure of the operative zone ambient environment 1 and decreasing that of the intravascular space, it is an object of the present invention to reduce and prevent said hemorrhage.

Figure 5:
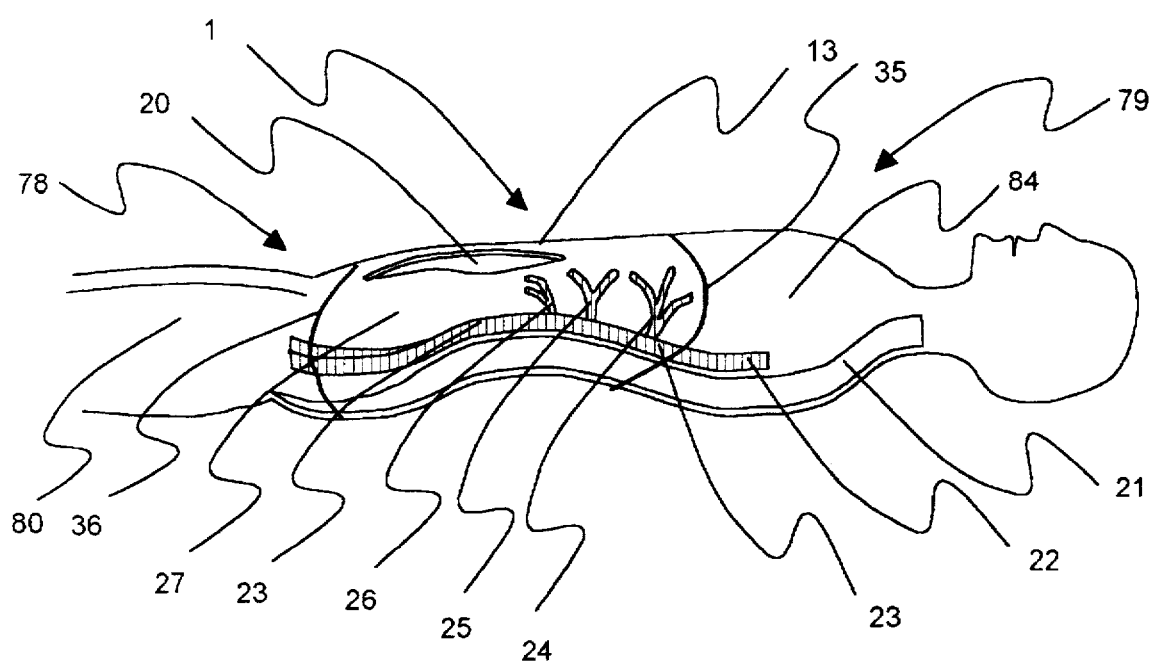
FIG. 5 is a sagittal cross section of an incised and opened abdomen.

FIG. 5 is a sagittal cross section of a body with an abdominal incision 20. The abdominal incision 20 could represent a general surgical abdominal incision or a traumatic wound and is shown to extend through the skin 13 and into the abdominal cavity 27. The walls of the abdominal vessels, including the abdominal aorta 23 and its branches, including the celiac trunk 24, the superior mesenteric artery 25, and the inferior mesenteric artery 26 provide tension to contain the blood against the pressure gradient from the intravascular space to the pressure of the operative zone ambient environment 1, the aforesaid operative zone transarterial pressure gradient. Compromise of the integrity of these or other blood vessels can result in hemorrhage. By controlling the said operative zone transvascular pressure gradients, by at least one of increasing the pressure of the operative zone ambient environment 1 and decreasing that of the intravascular space, it is an object of the present invention to reduce and prevent said hemorrhage. Reduction of the intravascular pressures may be accomplished by applying a reduced pressure to the proximal non-operative ambient environment 79, and this said reduced pressure is transmitted to the structures within the proximal non-operative body segment 84, including the descending thoracic aorta 22. The reduction in pressure of the blood within the descending thoracic aorta 22 is transmitted to the blood within the abdominal aorta 23. This will reduce the operative zone transarterial pressure gradients, facilitating decrease and elimination of arterial hemorrhage. Similarly, a reduction in the operative zone transvenous pressure gradient will result in alleviation or elimination of venous hemorrhage. This effect may be achieved intraoperatively and postoperatively. Additionally this effect may be achieved in preoperative or non-operative conditions, including but not limited to aortic rupture arising from aneurysms or dissections as well as trauma.

To maintain proper circulation and prevent vascular collapse in the portion of the distal body segment 80 which is distal to that exposed to the operative zone ambient environment 1, a negative pressure is applied to the distal non-operative ambient environment 78. This allows the maintenance of a perfusion pressure in the distal body segment 80 including that portion distal to the abdominal cavity caudal border 36. The negative pressure in the distal non-operative ambient environment 78 may be maintained at the same or a different negative pressure as compared to the proximal non-operative ambient environment 79. For example, the negative pressure in the distal non-operative ambient environment 78 may be maintained at a pressure more positive than either of the proximal non-operative ambient environment 79 or the operative zone ambient environment 1 to supplement venous return from the distal non-operative body segment 80. Further, the pressures of the proximal 79 and distal 78 non-operative environments may be cycled synchronously or independently. Additionally, the pressures of the proximal 79 and distal 78 non-operative environments may be maintained near that of the operative zone ambient environment 1 and brought to more negative pressures only as needed for intraoperative, perioperative, or other control of hemorrhage.

The same method of reducing hemorrhage may be achieved by applying a positive pressure to the operative zone ambient environment 1 to oppose hemorrhage driven by the operative zone transvascular pressure gradients present across the walls of the abdominal blood vessels, including those of the abdominal aorta 23 and its branches. Constant, cyclical, or intermittent pressure may be applied to the distal non-operative ambient environment 78 to supplement venous return from the distal body segment 80.

Figure 6:
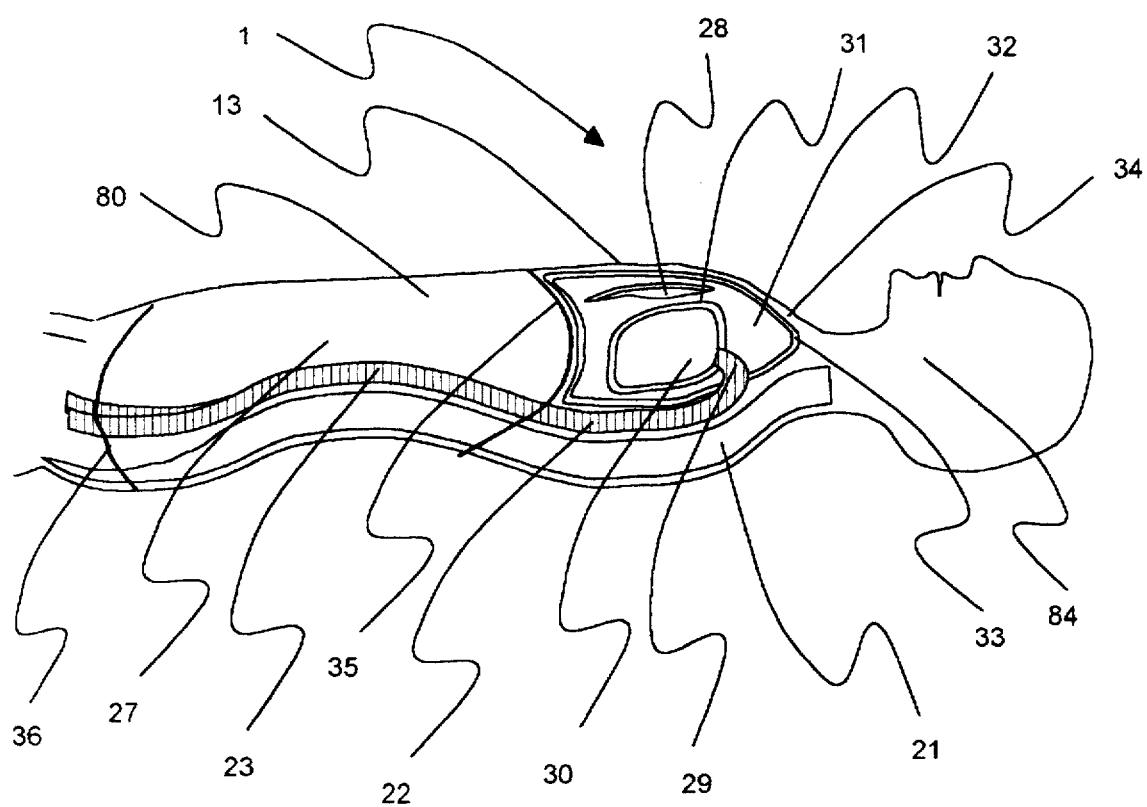
FIG. 6 is a sagittal cross section of an incised and opened thorax.

FIG. 6 is a sagittal cross section of a body with a thoracic wall incision, known as a thoracotomy 28. The thoracotomy 28 could represent a cardiothoracic or other surgical thoracic incision or a traumatic wound and is shown to extend through the skin 13 and may extent through the thoracic wall 34 into the thoracic cavity 33. The thoracic cavity 33 contains the lungs 32, heart 30, pericardium 31, ascending thoracic aorta 29, descending thoracic aorta 22, and other structures. The inferior border of the abdominal cavity 36, abdominal cavity 27, abdominal aorta 23, diaphragm 35, and vertebral column 21 are also shown. During thoracic and particularly cardiothoracic surgical procedures, significant hemorrhage may occur. The flow of blood during said hemorrhage is driven by the operative zone transvascular pressure gradients, the most pronounced including those across the walls of the heart 30, ascending aorta 29, and descending aorta 22.

By applying a negative pressure to the proximal non-operative body segment 79 and distal nonoperative body segment 80, the pressure developed by the heart 30 in the intrathoracic arterial structures including the ascending aorta 29 and descending aorta 22 and their many branches is reduced; consequently hemorrhage resulting from damage to any of these structures is lessened. By applying an equivalent positive pressure to the operative zone ambient environment 1, the same operative zone transvascular pressure gradients will be lessened; and the same reduction in hemorrhage is achieved.

Figure 7:
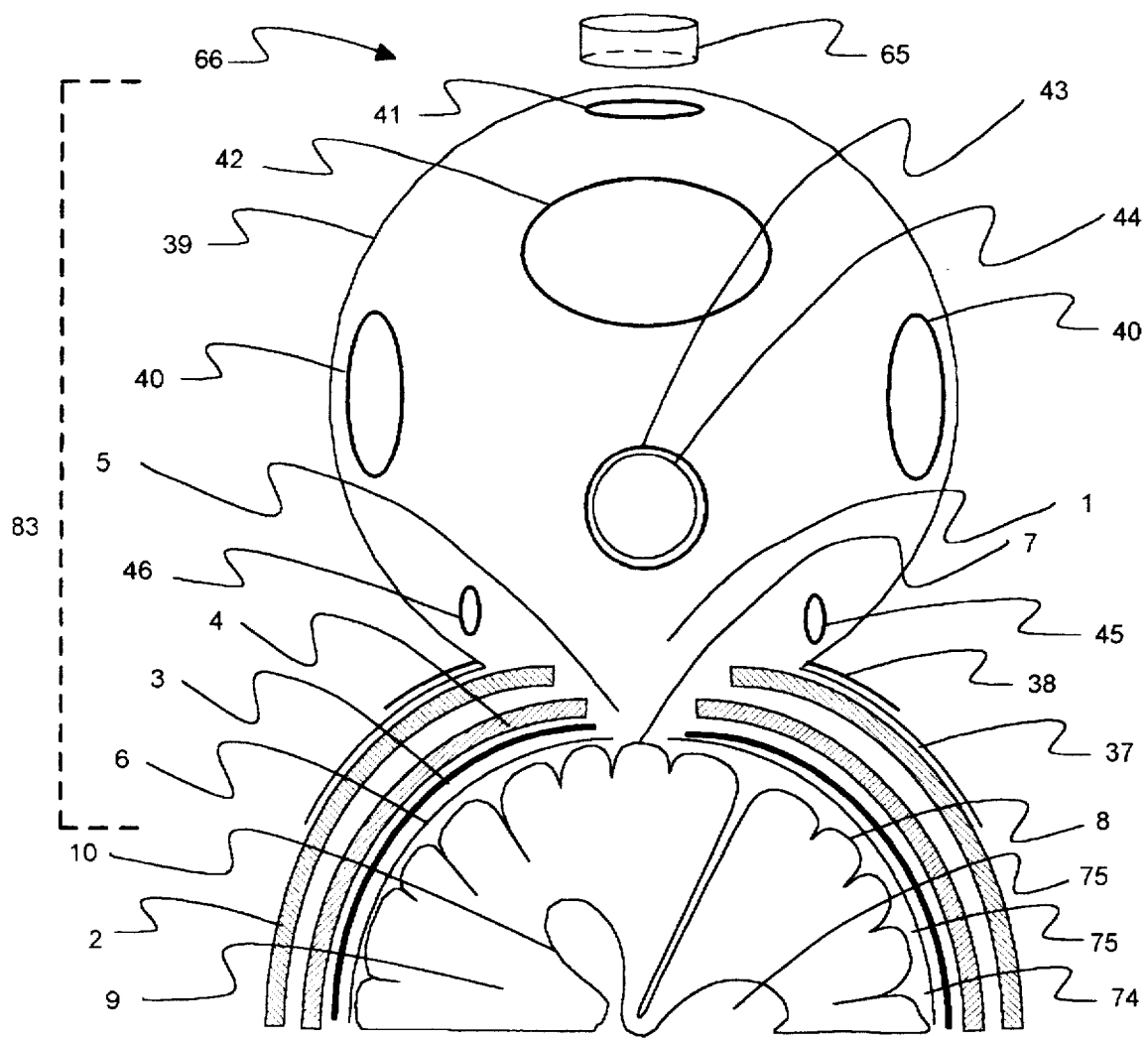
FIG. 7 is a coronal cross section of the brain with an operative zone ambient positive pressure applying apparatus in position about a craniotomy.

FIG. 7 depicts an apparatus for executing the method of performing a craniotomy with reduced cerebral edema, hemorrhage, and movement as illustrated in FIG. 1 by the application of positive pressure to the operative zone ambient environment 1 contained within the pressurized chamber 83. The positive pressure in the operative zone ambient environment 1 may be selected to reduce, eliminate, or reverse the intracranial pressure gradient otherwise born by the exposed cortical surface 7 and the underlying brain parenchyma 9. Although the craniotomy 5 is depicted over the cerebral cortex, the present invention applies to any portion of the central nervous system, including the cerebrum, cerebellum, and brainstem.

A flexible membrane 39 encloses the operative zone ambient environment 1. The flexible membrane 39 could be replaced with a rigid or semirigid structure without departing from the spirit of the present invention. The flexible membrane 39 is attached to the scalp 2 by a flange 37 surrounding the region of the craniotomy 5. The flange 37 may be secured to the scalp 2 by at least one of an adhesive, mechanical force, a combination, or other means. A flange restrainer 38 prevents peeling of the flange 37 away from the scalp 2, particularly in the region where the flange 37 joins the flexible membrane 39. The positive pressure of the operative zone ambient environment 1 within the flexible membrane 39 is maintained by a positive fluid pressure applied to the inflow port 45. An outflow port 46 may be included to permit circulation of fluid within the operative zone ambient environment 1, facilitating control of the state of the fluid, including temperature, humidity, composition, and other variables in addition to pressure.

Glove ports 40 are provided to allow access to the operative zone by the surgeon and other operating room or trauma personnel. The said glove ports 40 may have gloves and sleeves permanently or temporarily attached. Alternatively, the glove ports 40 may include seal means to facilitate insertion of gloved hands. A passage portal 43 is provided to allow insertion and retrieval of instruments, tissues, and other objects between the non-operative zone ambient environment 66 and the operative zone ambient environment 1. A passage portal closure means 44 is attached to the said passage portal 43 and allows for the maintenance of a fluid tight seal surrounding the operative zone ambient environment 1. The flexible membrane 39 may be constructed from a transparent material. A window 42 is constructed from a rigid or flexible transparent material to augment visualization of the operative zone. A multiplicity of windows 42 may be included without departing from the spirit of the present invention. A microscope port 41 is connected to the flexible membrane 39 to facilitate unimpeded visualization of the operative zone via a surgical microscope 65. Also shown are the dura 3, calvarum 4, arachnoid 6, unexposed cortical surface 8, brain parenchyma 9, and the cerebrospinal fluid 75 which occupies the ventricles 10 and subarachnoid space 74 among other structures.

Figure 8:
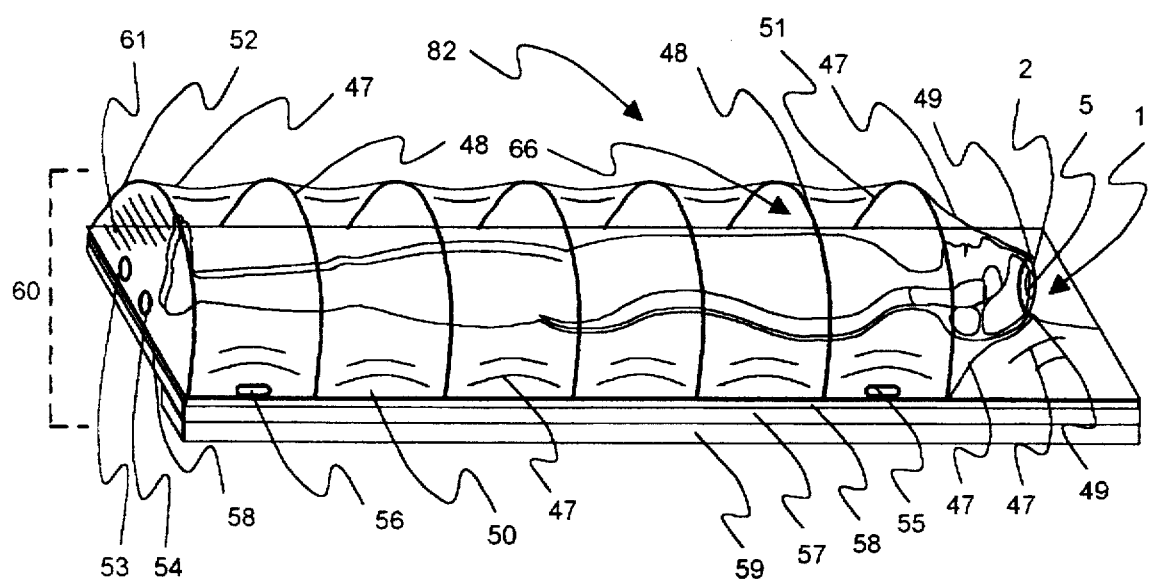
FIG. 8 is a lateral view of a non-operative zone ambient negative pressure applying flexible apparatus in position about a craniotomy.

FIG. 8 depicts an apparatus for executing the method of performing a craniotomy with reduced cerebral edema, hemorrhage, and movement as illustrated in FIG. 1 by the application of negative pressure to the non-operative zone ambient environment 66 which is contained within the partially evacuated chamber 60. Application of a negative pressure to the non-operative zone ambient environment 66 effects an absolute decrease in the hydrostatic pressures of all contained bodily regions in communication with the skin exposed to the said non-operative ambient environment 66. By this method, the depicted apparatus allows precise control of the intracranial pressure; the intracranial pressure may be reduced to approach, equal, or fall below the pressure of the operative zone ambient environment 1. Although the craniotomy 5 is depicted over the cerebral cortex, the present invention applies to any portion of the central nervous system, including the cerebrun, cerebellum, and brainstem.

A flexible membrane 47 forms the top and lateral sides of the partially evacuated chamber 60 which contains the non-operative zone ambient environment 66. The flexible membrane 47 is supported against the pressure of the room ambient environment 82 by at least one of a cephalic membrane support 51, caudal membrane support 52, and intermediate membrane supports 48. A membrane to craniotomy operative zone seal means 49 maintains a fluid tight seal between the flexible membrane 47 and the scalp 2 surrounding the region of the craniotomy 5. The partially evacuated chamber caudal side 61 may be a continuation of the flexible membrane 47 and may be constructed from a rigid or semirigid material without departing from the spirit of the present invention.

One or a multiplicity of low pressure gas outflow ports 53 facilitates partial evacuation of gas from the partially evacuated chamber 60. One or a multiplicity of low pressure gas inflow ports 54 may be included to allow circulation of gas in the said partially evacuated chamber 60, facilitating control of the temperature, humidity, composition, and other properties in addition to pressure. One or a multiplicity of injection fluid inflow ports 55 may be included to provide access for intravenous, intramuscular, subdural, epidural, or other fluid lines. One or a multiplicity of bodily fluid outflow ports 56 may be included to provide access for urine, blood sampling, and other lines. The said low pressure gas outflow port 53 and low pressure gas inflow port 54 are shown attached to the partially evacuated chamber caudal side 61; this location is exemplary and could be interchanged with any side of the said partially evacuated chamber 60, including any portion of the flexible membrane 47 or the partially evacuated chamber bottom side 50. Similarly, the locations of the injection fluid inflow ports 55 and bodily fluid outflow ports 56 may be altered without departing form the spirit of the present invention.

The flexible membrane 47 may be supplied as a discrete sheet or continuous roll withdrawn from a membrane dispenser means 59 shown mounted to the partially evacuated chamber bottom side 50. A membrane to chamber bottom seal means 58 provides a fluid tight seal between the flexible membrane 47 and the partially evacuated chamber bottom side 50 and is shown attached to the lateral aspect 57 of the partially evacuated chamber bottom side 50. The said membrane to chamber bottom seal means 58 may equivalently be attached to any aspect of the said partially evacuated chamber bottom side 50, and the said partially evacuated chamber bottom side 50 may include, be attached to, or be separate from the operating room table without departing from the spirit of the present invention.

Figure 9:
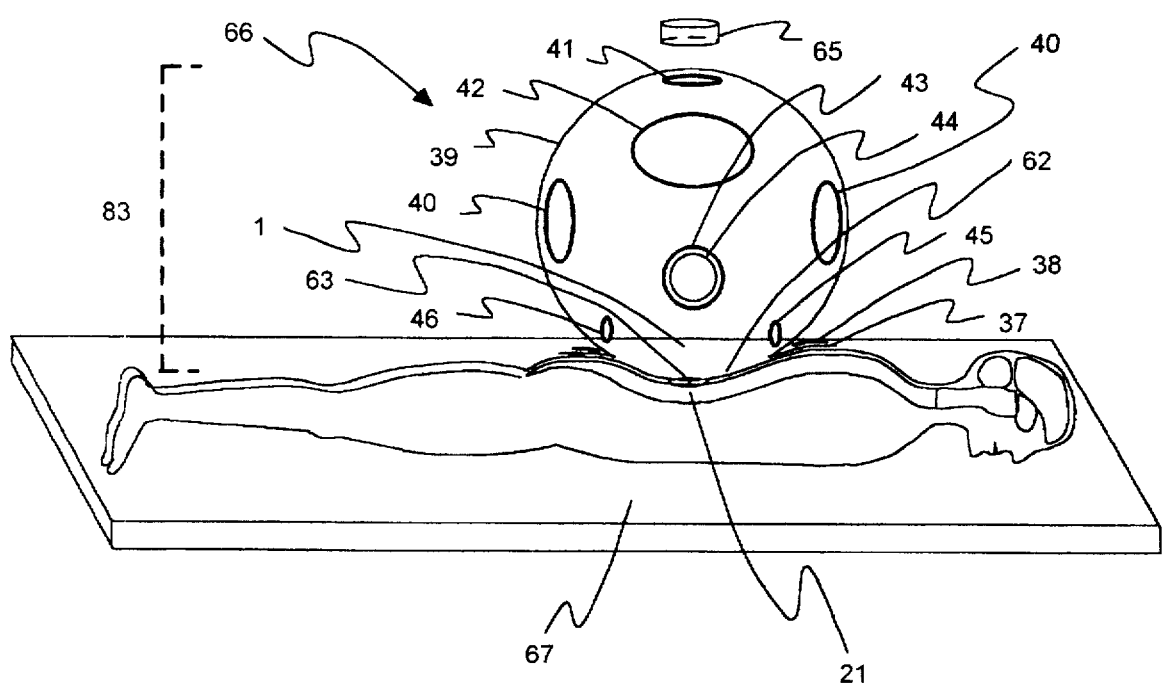
FIG. 9 is a lateral view of an operative zone ambient positive pressure applying apparatus in position about a spinal procedure.

FIG. 9 depicts an apparatus for executing the method of performing a spinal procedure with reduced spinal cord edema, hemorrhage, and movement as illustrated in FIG. 2 by the application of positive pressure to the operative zone ambient environment 1 contained within the pressurized chamber 83. The positive pressure in the operative zone ambient environment 1 may be selected to reduce, eliminate, or reverse the pressure gradient, substantially identical to the intracranial pressure, otherwise born by the spinal cord surface 77 and the underlying spinal cord parenchyma 76.

The back incision 63 and the underlying laninectomy 12 (see FIG. 2) are in contact with the operative zone ambient environment 1 which is contained within the pressurized chamber 83 and maintained at a pressure greater than that of the non-operative zone ambient environment 66. The flange 37 is affixed to the back skin 62 by at least one of an adhesive, mechanical pressure, clamps, or other means. The flange restrainer 38 prevents peeling of the flange 37 away from the back skin 62 which might otherwise occur at the junction of the flange 37 and the flexible membrane 39. The flange 37 is depicted as flexible and the flange restrainer 38 as rigid; however, this is exemplary, and the said flange 37 and flange restrainer 38 may be combined into a single flexible or rigid flange means without departing from the spirit of the present invention.

The remaining components of the said pressurized chamber 83 of FIG. 9 are substantially equivalent to those described in detail in the description of FIG. 7. The patient is shown lying prone atop the operating table 67; blankets, pads, and other operating room accessories are omitted for clarity.

Figure 10:
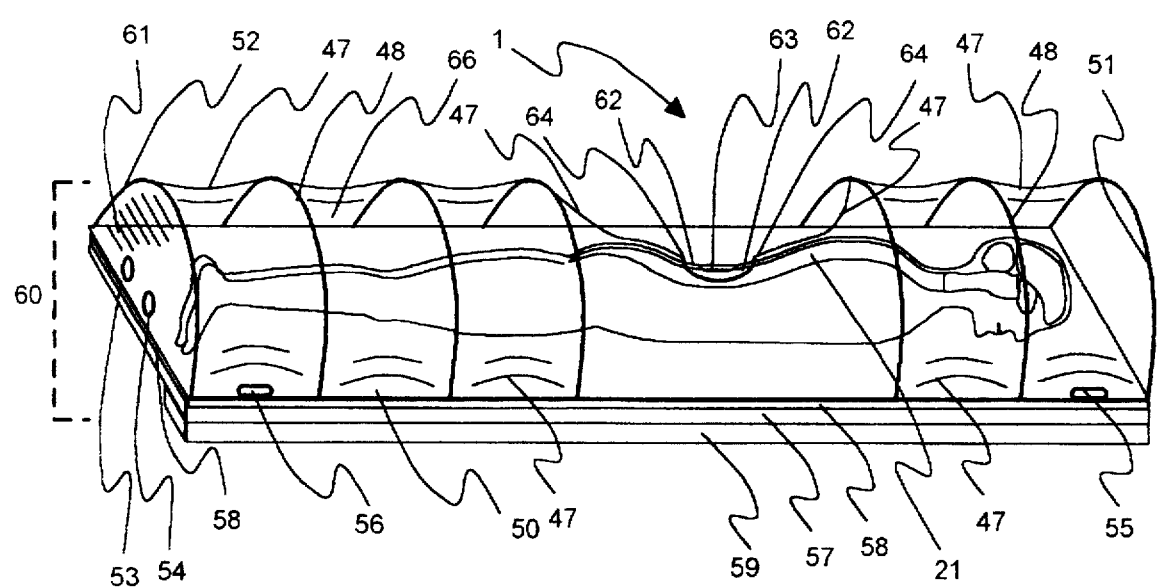
FIG. 10 is a lateral view of a non-operative zone ambient negative pressure applying flexible apparatus in position about a spinal procedure.

FIG. 10 depicts an apparatus for executing the method of performing a spinal procedure with reduced spinal cord edema, hemorrhage, and movement as illustrated in FIG. 2 by the application of negative pressure to the non-operative zone ambient environment 66 contained within the partially evacuated chamber 60.

Application of a negative pressure to the non-operative zone ambient environment 66 effects an absolute decrease in the hydrostatic pressures of all contained bodily regions which are in communication with the skin exposed to the said non-operative zone ambient environment 66. By this method, the depicted apparatus allows precise control of the intracranial pressure, which is substantially equivalent to that of the spinal cord parenchyma 76 and the cerebrospinal fluid 75. The intracranial pressure may be reduced to approach, equal, or fall below the pressure of the operative zone ambient environment 1. The pressure gradients driving edema formation, hemorrhage, and spinal cord tissue movement may thus be eliminated. Modulation of the negative pressure within the partially evacuated chamber 60 in relation to the respiratory or ventilatory cycle reduces and prevents the movement of the nervous tissue which is otherwise observed to occur in synchrony with the respiratory cycle.

The membrane to back operative zone seal means 64 provides a fluid tight seal between the flexible membrane 47 and the back skin 62 surrounding the back incision 63. The remaining components of the said partially evacuated chamber 60 of FIG. 10 are substantially equivalent to those described in detail in the description of FIG. 8. The patient is shown lying prone atop the partially evacuated chamber bottom side 50, which may be attached to or identical to the operating table 67. Alternatively, the patient could be lying on the operating table 67 which may be attached to or separate from the partially evacuated chamber bottom side 50; blankets, pads, and other operating room accessories are omitted for clarity.

Figure 11:
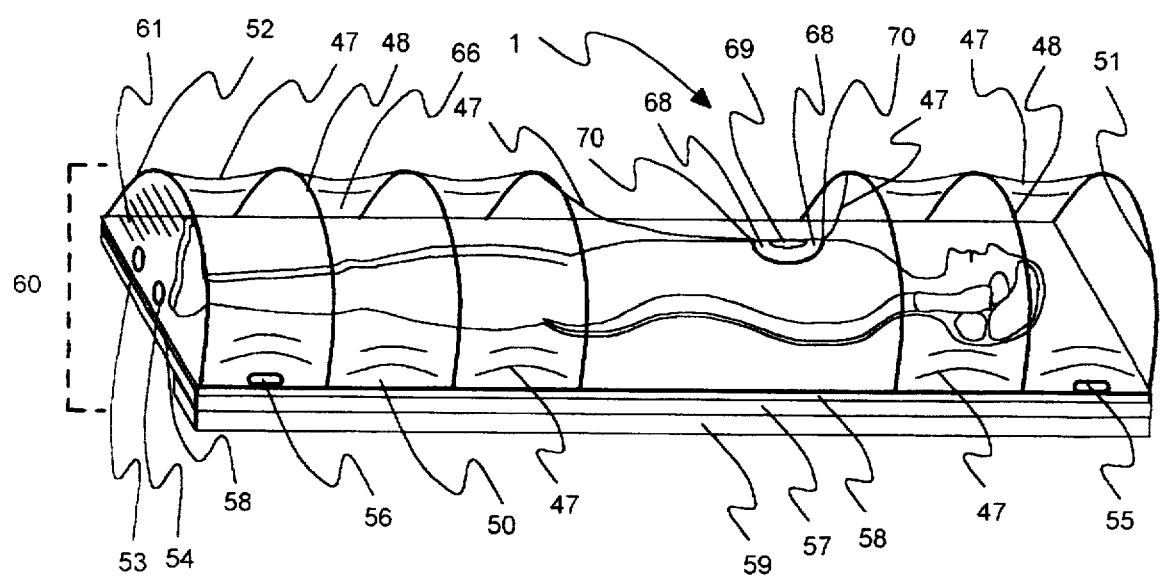
FIG. 11 is a lateral view of a non-operative zone ambient negative pressure applying flexible apparatus in position about a thoracotomy.

FIG. 11 depicts an apparatus for executing the method of performing a surgical procedure involving a thoracotomy with reduced hemorrhage as illustrated in FIG. 6 by the application of negative pressure to the non-operative zone ambient environment 66 contained within the partially evacuated chamber 60.

Application of a negative pressure to the non-operative zone ambient environment 66 effects an absolute decrease in the hydrostatic pressures of all contained bodily regions which are in communication with the skin exposed to the said non-operative zone ambient environment 66. By this method, the depicted apparatus allows precise control of the pressure of the venous blood returning to the heart 30 (see FIG. 6) and some control of the back pressure applied to the pumping heart 30 (see FIG. 6) via the arterial blood contained in the ascending aorta 29 (see FIG. 6). The operative zone transvascular pressure gradients driving arterial and venous hemorrhage may thus be reduced or eliminated.

The membrane to thoracotomy operative zone seal means 70 provides a fluid tight seal between the flexible membrane 47 and the thorax skin 68 surrounding the thoracotomy 69. The remaining components of the said partially evacuated chamber 60 of FIG. 10 are substantially equivalent to those described in detail in the description of FIG. 8. The patient is shown lying supine atop the partially evacuated chamber bottom side 50, which may be attached to or identical to the operating table 67. Alternatively, the patient could be lying on the operating table 67 which may be attached to or separate from the partially evacuated chamber bottom side 50; blankets, pads, and other operating room accessories are omitted for clarity.

Figure 12:
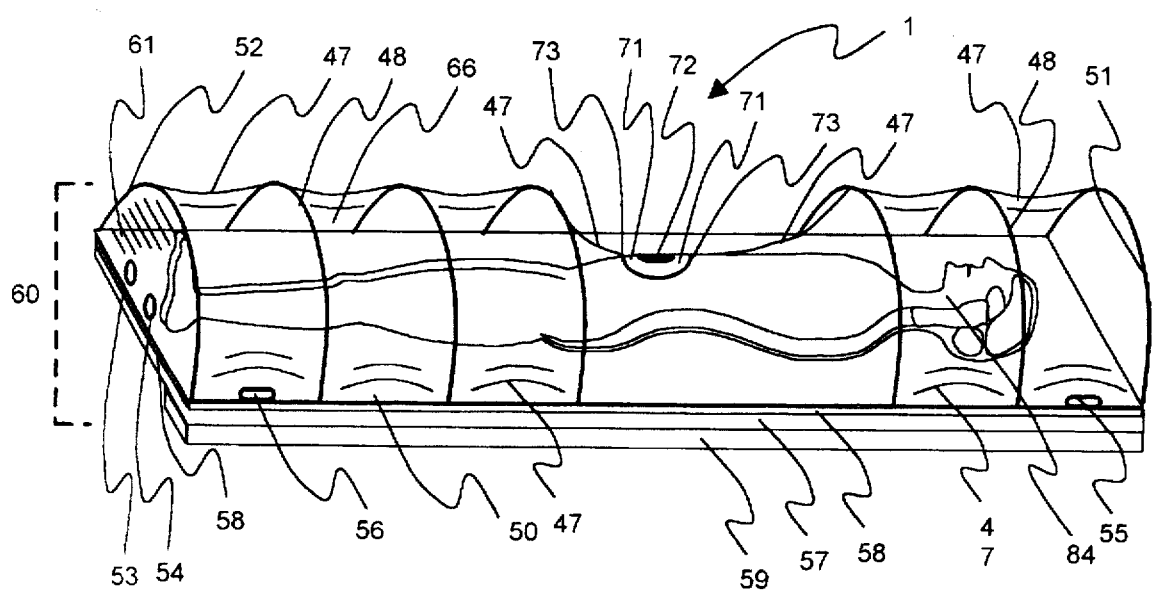
FIG. 12 is a lateral view of a non-operative zone ambient negative pressure applying flexible apparatus in position about an abdominal procedure.

FIG. 12 depicts an apparatus for executing the method of performing a surgical procedure involving an abdominal incision with reduced hemorrhage as illustrated in FIG. 5 by the application of negative pressure to the non-operative zone ambient environment 66 contained within the partially evacuated chamber 60.

Application of a negative pressure to the non-operative zone ambient environment 66 effects an absolute decrease in the hydrostatic pressures of all contained bodily regions which are in communication with the skin exposed to the said non-operative zone ambient environment 66. By this method, the depicted apparatus allows precise control of the absolute pressure of the arterial blood within the descending thoracic aorta 22 (see FIG. 5) in the proximal non-operative body segment 84 which is contained within the non-operative ambient environment 66. The arterial blood within the descending thoracic aorta 22 (see FIG. 5) passes through the diaphragm 35 (see FIG. 5) into the abdominal aorta 23 (see FIG. 5) within the abdominal cavity 27 (see FIG. 5). The pressure of the blood within the abdominal aorta 23 (see FIG. 5) may be controlled by manipulating the partial vacuum applied to the proximal non-operative body segment 84 to regulate the pressure of the blood within the descending thoracic aorta 23 (see FIG. 5).

Hemorrhage is driven by the operative zone transvascular pressure gradients, such as that between the abdominal aorta 23 (see FIG. 5) and the operative zone ambient environment 1. By regulating the pressure of the blood within these vessels, according to the present invention, hemorrhage may be controlled or eliminated.

The membrane to abdomen operative zone seal means 73 provides a fluid tight seal between the flexible membrane 47 and the abdominal skin 71 surrounding the abdominal incision 72. The remaining components of the said partially evacuated chamber 60 of FIG. 10 are substantially equivalent to those described in detail in the description of FIG. 8. The patient is shown lying supine atop the partially evacuated chamber bottom side 50, which may be attached to or identical to the operating table 67. Alternatively, the patient could be lying on the operating table 67 which may be attached to or separate from the partially evacuated chamber bottom side 50; blankets, pads, and other operating room accessories are omitted for clarity.

Figure 13:
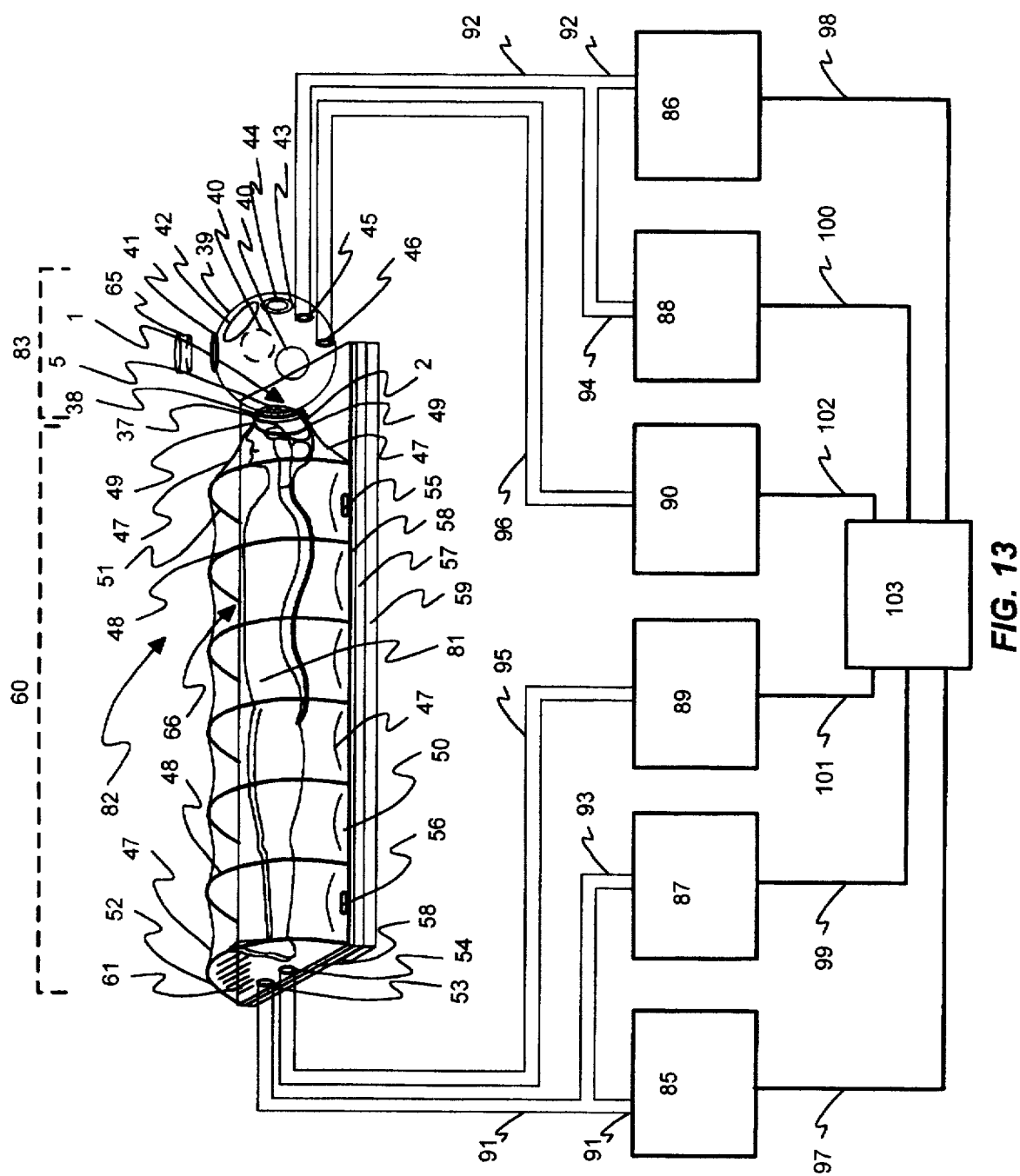
FIG. 13 is a lateral view of the apparatus system including the non-operative zone ambient negative pressure applying flexible apparatus and operative zone ambient positive pressure applying apparatus in position about a craniotomy.

FIG. 13 depicts a system according to the present invention for executing the method of manipulating tissue pressure gradients for use in controlling at least one of fluid flow and tissue movement intraoperatively, postoperatively, preoperatively, or post-traumatically. The system controls the pressure gradient between a subject and an environment. The figure provides an example the application of this invention to a neurosurgical procedure involving a craniotomy 5; in this application, the device controls the transdural pressure gradient between the intracranial pressure present in the brain parenchyma 9 (see FIG. 1) and the operative zone ambient environment 1. The said pressure gradient is manipulated by the difference between the pressure of the operative zone ambient environment 1 contained within the pressurized chamber 83 and the pressure of the non-operative zone ambient environment 66 contained within the partially evacuated chamber 60. An obvious simplification of this system is the omission of one of the said chambers. In this case, the said pressure gradient is manipulated by the difference between the pressure of the single chamber and the pressure of the room ambient environment 82. Other variations of the present invention include the use of rigid or semirigid materials in the construction of either of the said hermetic chambers. Further, the said hermetic chambers could be constructed as portable devices, fixed stations, as regions within the operating room separated by at least one partition, as separate rooms, or other variation of the present invention.

Pressure sources 85 and 86 separately provide fluid at a pressure, said pressure may be but is not restricted to be set according to: a predetermined value, a predetermined time-varying profile, a timevarying profile determined in realtime, a manually determined value or profile, a dynamic profile determined as a function of variables including but not limited to vital functions and pressure gradients.

In the application depicted, pressure source 85 applies a partial vacuum or hypobaric pressure, and pressure source 86 applies a hyperbaric pressure. Pressure source 85 is connected via fluid outlet hose 91 to low pressure gas outflow port 53. Outflow fluid sensor 87 is connected via fluid sensor hose 93 to fluid outlet hose 91 and senses pressure and other fluid characterization values of the fluid emanating from the partially evacuated chamber 60. Inflow fluid sensor 89 is connected via fluid inlet hose 95 to low pressure gas inflow port 54. Inflow fluid sensor 89 can be employed to sense characteristics if inflowing fluid; alternatively, if inflow is blocked, said inflow fluid sensor 89 can be employed to sense the pressure within partially evacuated chamber 60. Pressure source 86 is connected via fluid inlet hose 92 to fluid inflow port 45. Inflow fluid sensor 88 is connected via fluid sensor hose 94 to fluid inlet hose 92 and senses pressure and other fluid characterization values of the fluid flowing into the pressurized chamber 83. Outflow fluid sensor 90 is connected via fluid outlet hose 96 to fluid outflow port 46. Outflow fluid sensor 90 can be employed to sense characteristics if outflowing fluid; alternatively, if outflow is blocked, said outflow fluid sensor 90 can be employed to sense the pressure within pressurized chamber 83.

The pressure gradient between the exposed cortical surface 7 (see FIG. 1) of the operative subject 81 and the operative zone ambient atmosphere 1 is controlled by controller 103. The controller 103 is connected to at least one of pressure source 85 via data link 97, pressure source 86 via data link 98, outflow fluid sensor 87 via data link 99, inflow fluid sensor 88 via data link 100, inflow fluid sensor 89 via data link 101, and outflow fluid sensor 90 via data link 102. The said controller 103 may include a means to estimate the operative tissue-ambient pressure gradient, for example the transdural pressure gradient as illustrated in FIG. 13. The controller 103 may maintain the operative tissue-ambient pressure gradient according to any constant or time-varying profile, including but not restricted to a preset value or series thereof, a single or series of values determined intraoperatively, a manually set value or series thereof, a single or series of values which are a function of a combination of at least one of measured or estimated values, a single or series of values determined according to bodily parameters or functions, and a series of values determined according to a control law.

Furthermore, as applied to all methods and apparatus discussed heretofore, including the partially evacuated chambers 60 and the pressurized chambers 83, intermittent variation in the pressures within the respective said chambers will facilitate intermittent hemorrhage. This may be desired to enable the surgeon to identify and correct potential intraoperative or postoperative sources of hemorrhage.

It is understood that modifications to the invention as described may be made, as might occur to one with skill in the field of the invention, within the intended scope of the claims. Therefore, all embodiments contemplated have not been shown in complete detail. Other embodiments may be developed without departing from the spirit of the invention or from the scope of the claims.

What is claimed and desired to be secured by Letters Patent is:

1. A surgical procedure for maintaining intracranial pressure on a human patient comprising:

creating a surgical incision in the human scalp which penetrates up to the surface of a human brain;

placing a container in surrounding relationship to the incision, and sealing the container to portions of the human scalp immediately adjacent to the incision so as to create an enclosed space between the scalp and the container, said container further including means for pressurizing the enclosed space and means for accessing the enclosed space and incision;

raising the pressure in the enclosed space to at least 14 mmHG so as to reduce the pressure gradient between the intracranial pressure and the local ambient pressure.

2. A surgical procedure for reducing spinal cord edema comprising:

creating a surgical incision in the region of the spinal cord which penetrates up to the surface of the spinal cord;

placing a container in surrounding relationship to the incision, and sealing the container to a skin surface immediately adjacent to the incision so to create an enclosed space between a skin surface and the container, said container further including means for pressurizing the enclosed space and means for accessing the enclosed space and incision;

raising the pressure in the enclosed space to at least 14 mm HG so as to reduce the pressure gradient between the spinal cord and the local ambient pressure.

* * * * *